(12) United States Patent
Schmidt

(10) Patent No.: US 6,361,802 B1
(45) Date of Patent: Mar. 26, 2002

(54) METHOD AND APPARATUS FOR THE RECOVERY OF NON-SOLVENT TYPE FILLS FROM GELATIN CAPSULES

(75) Inventor: William J. Schmidt, Dresher, PA (US)

(73) Assignee: A.B. Technologies Holding, L.L.C.

( * ) Notice: Subject to any disclaimer, the term of this patent is extended or adjusted under 35 U.S.C. 154(b) by 0 days.

(21) Appl. No.: 09/609,217

(22) Filed: Jul. 5, 2000

Related U.S. Application Data

(60) Provisional application No. 60/144,154, filed on Jul. 15, 1999, and provisional application No. 60/193,440, filed on Mar. 30, 2000.

(51) Int. Cl.$^7$ ............ A61K 35/78; A61K 9/64; B01D 35/18; C07K 1/00
(52) U.S. Cl. .............. 424/725; 424/456; 210/634; 210/774; 530/355
(58) Field of Search ................. 424/725, 456; 210/634, 774; 530/355

(56) References Cited

U.S. PATENT DOCUMENTS

| | | | |
|---|---|---|---|
| 3,800,399 A | * | 4/1974 | Warrick et al. |
| 4,478,118 A | * | 10/1984 | Lightner |
| 5,074,102 A | | 12/1991 | Simpson et al. |
| 5,288,408 A | * | 2/1994 | Schmidt et al. |
| 5,945,001 A | | 8/1999 | Schmidt |

OTHER PUBLICATIONS

Munir Cheryan, Ph.D., "Ultrafiltration Handbook", 1986, pp. 276–277.

J. Schwennen, GEA Westfalia Separator AG, "Separators and decanters for gelatine production", pp. 2–14, May 1999.

* cited by examiner

*Primary Examiner*—Christopher R. Tate
(74) *Attorney, Agent, or Firm*—Watov & Kipnes, P.C.

(57) ABSTRACT

Method and apparatus for recovering non-solvent fills from a gelatin-containing material by adding the gelatin-containing material to a suitable solvent to form a mixture including a solvent phase and a phase containing said non-solvent fill and then separating the solvent phase from the phase containing said non-solvent fill, followed by recovering the non-solvent fill.

20 Claims, 4 Drawing Sheets

METHOD AND APPARATUS FOR THE RECOVERY OF NON-SOLVENT TYPE FILLS FROM GELATIN CAPSULES

RELATED APPLICATION

This application claims the benefit of U.S. Provisional Patent Application Ser. No. 60/144,154 filed on Jul. 15, 1999 and U.S. Provisional Patent Application Ser. No. 60/193,440 filed on Mar. 30, 2000.

FIELD OF THE INVENTION

The present invention is directed to a process for the recovery of non-aqueous type fills from gelatin capsules including hard and soft gelatin capsules in which the capsules are heated with a suitable solvent (e.g. water) until the capsules dissolve and separate into a lower solvent phase containing solvent, gelatin, plasticizer and, if applicable, solvent soluble dyes and other solvent soluble components and an upper non-solvent phase containing the non-solvent fill. The two phases are separated and the non-solvent phase may be further processed to remove any residual solvent and the solvent phase may be further processed to recover the gelatin, plasticizer and, if applicable, dyes and other solvent soluble components.

BACKGROUND OF THE INVENTION

Methods for recovering non-solvent type fills (e.g. non-aqueous fills as referred to hereinafter) from hard and soft gelatin materials, typically in the form of capsules, are known in the art. Such methods are inefficient and are generally only applicable to recovery of a few fills such as vitamin E. A typical prior art method includes chopping capsules into fine pieces and allowing the non-aqueous fill to either drip off the chopped capsules by gravity or, alternatively, vacuum is applied to the chopped capsules and the recovered non-aqueous fill collected. As used herein, the term capsules refers to any capsules obtained from a capsule producing process which are not saleable for reasons including, but not limited to, cloudiness, malformation, incorrect fill quantity, or expired commercial lots returned to the manufacturer.

Such prior art methods achieve only from about 30% to 70% recovery of the non-aqueous fill, principally due to the viscous nature of the recoverable material.

It would be a significant benefit in the art of removing non-solvent fills (e.g. non-aqueous fills) from gelatin capsules to improve the recovery of the non-aqueous fill, and especially for a process having recovery rates consistently exceeding 90%.

SUMMARY OF THE INVENTION

The present invention is generally directed to a process and apparatus for recovering non-solvent type fills (e.g. non-aqueous type fills as referred to hereinafter) from a gelatin-containing material, typically in the form of capsules including hard and soft gelatin capsules, in a cost efficient and effective manner.

In a particular aspect of the present invention there is provided a method and apparatus for recovering non-solvent fills from a gelatin-containing material comprising:

a) adding the gelatin-containing material to a suitable solvent to form a mixture including a solvent phase and a phase containing said non-solvent fill;

b) separating the solvent phase from the phase containing said non-solvent fill; and c) recovering the non-solvent fill.

The process more specifically comprises adding gelatin capsules, with or without prior "grinding" thereof, to a suitable solvent (e.g. deionized water) typically in an amount of up to 5.0 volumes wt/wt, preferably from about 0.5 to 3 volumes wt/wt based on the quantity of capsules being processed. The addition step is typically carried out in a vessel at a temperature from about 40° C. to 70° C. with agitation, preferably by using a sweep mixer which is incorporated into the apparatus illustrated in FIGS. 2 and 3, at typically from about 5 rpm to 40 rpm to facilitate release of any residual non-aqueous fill from the aqueous phase and/or to homogenize the aqueous phase for enhanced processing. The above recited temperature and agitation are maintained until the capsules at least substantially dissolve which typically takes from about 15 to 60 minutes.

After dissolution, while maintaining the vessel temperature at from about 40° C. to 70° C. agitation is stopped and the dissolved capsules are allowed to at least substantially separate into a lower aqueous phase containing water, gelatin, plasticizer and, if applicable, dyes and other water soluble components and an upper phase containing the non-aqueous fill.

The separation may be achieved in any conventional manner including physical separation via a sight glass, using an apparatus such as that illustrated in FIG. 2, or through a mechanical skimmer such as an oil skimmer. The separation can also take place through various mechanical techniques such as, but not limited to, liquid-liquid centrifugation. Alternatively, the lower aqueous phase may be cooled and solidified and the non-aqueous phase collected by decanting or pouring from the top of the vessel using an apparatus such as that illustrated in FIG. 3.

The non-aqueous phase thus separated may be further processed to remove any residual water, especially if the fill is hygroscopic. This optional step may be conducted, for example, by treating the non-aqueous phase with molecular sieves or drying agents such as, but not limited to, magnesium sulfate. Other methods to remove the residual water from the non-aqueous phase include heating the non-aqueous material at or about atmospheric pressure, or under vacuum using an apparatus such as that illustrated in FIG. 4, preferably operating at a pressure of from 22 inches to about 29 inches of vacuum, at a temperature from about 40° C. to 105° C. for a period of time sufficient to remove the residual water, typically from about 30 minutes to 24 hours, to form an at least substantially dried non-aqueous phase.

The thus recovered non-aqueous fill may then be filtered, to remove any residual particulate matter which may be present, and reused in the capsule filling process. The aqueous phase may be optionally processed to recover the gelatin and plasticizer and, if applicable, dyes and other water soluble components so that these components may be recycled as well.

BRIEF DESCRIPTION OF THE DRAWINGS

The following drawings illustrate an embodiment of the invention and are not intended to limit the application as encompassed by the claims forming part of the application.

DETAILED DESCRIPTION OF THE INVENTION

Figure 1:
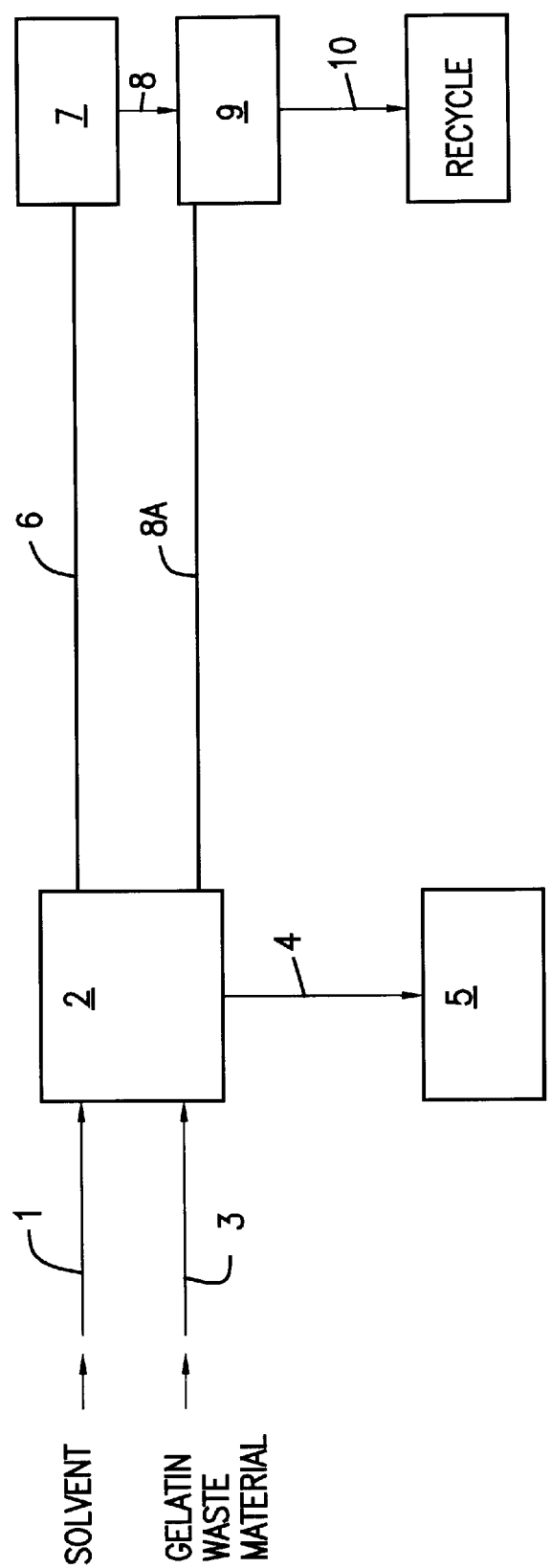
FIG. 1 is a schematic view of an embodiment of the method of non-aqueous fill recovery provided in accordance with the present invention.

Referring to FIG. 1, there is shown a process flow diagram wherein a suitable solvent (e.g. deionized water), in an amount of up to 5.0 volumes wt/wt, preferably from about 0.5 to 3 volumes wt/wt, to the quantity of capsules being processed, is charged via conduit 1 to a vessel 2. Vessel 2 is preferably constructed of stainless steel and, depending on the non-aqueous fill to be processed, may be a design such as that illustrated in FIGS. 2 and 3 as described in detail hereinafter.

Figure 2:
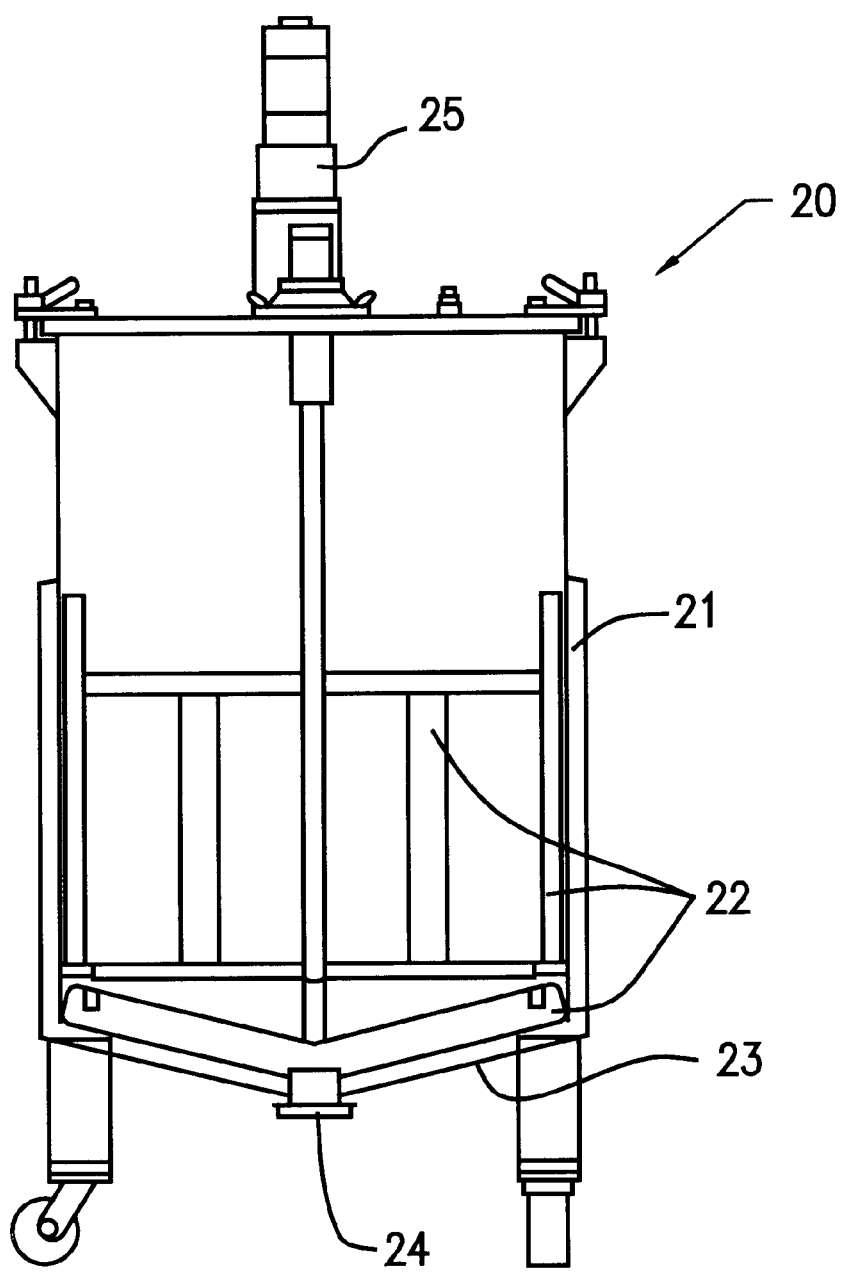
FIGS. 2 through 4 are side views in cross-section of an apparatus which may be employed in the present invention.

FIG. 2 illustrates an apparatus that may be utilized to process non-aqueous fills that contain dissolved and/or suspended solids such as, for example, co-enzyme Q10 in soy oil. It will be understood that all reference to "non-aqueous" fills is exemplary of fills that are not soluble in the solvent (e.g. water) chosen for operation of the recovery process. Other solvents and corresponding other fills may be employed in the present invention.

The apparatus 20 is equipped with a heating/cooling jacket 21 to approximately two-thirds of the vessel height; to apply heat primarily to the aqueous phase during processing. This jacket configuration may be desirable in the event the non-aqueous fill being processed has some degree of thermal sensitivity. The apparatus 20 is also equipped with a sweep mixer 22 designed in such a manner to perform a variety of functions including, but not limited to, dislodging molten gelatin from the walls and bottom of the vessel, homogenizing the aqueous phase for ease of processing/separating the aqueous phase, and dislodging residual non-aqueous fill trapped in residual molten gelatin. Additionally, the preferred mixer motor 25 is designed to operate at low speed. The apparatus 20 is also designed with a sloped bottom 23 and bottom center discharge 24 for enhanced separation of the aqueous and non-aqueous phases to minimize aqueous phase contamination of the non-aqueous phase.

Figure 3:
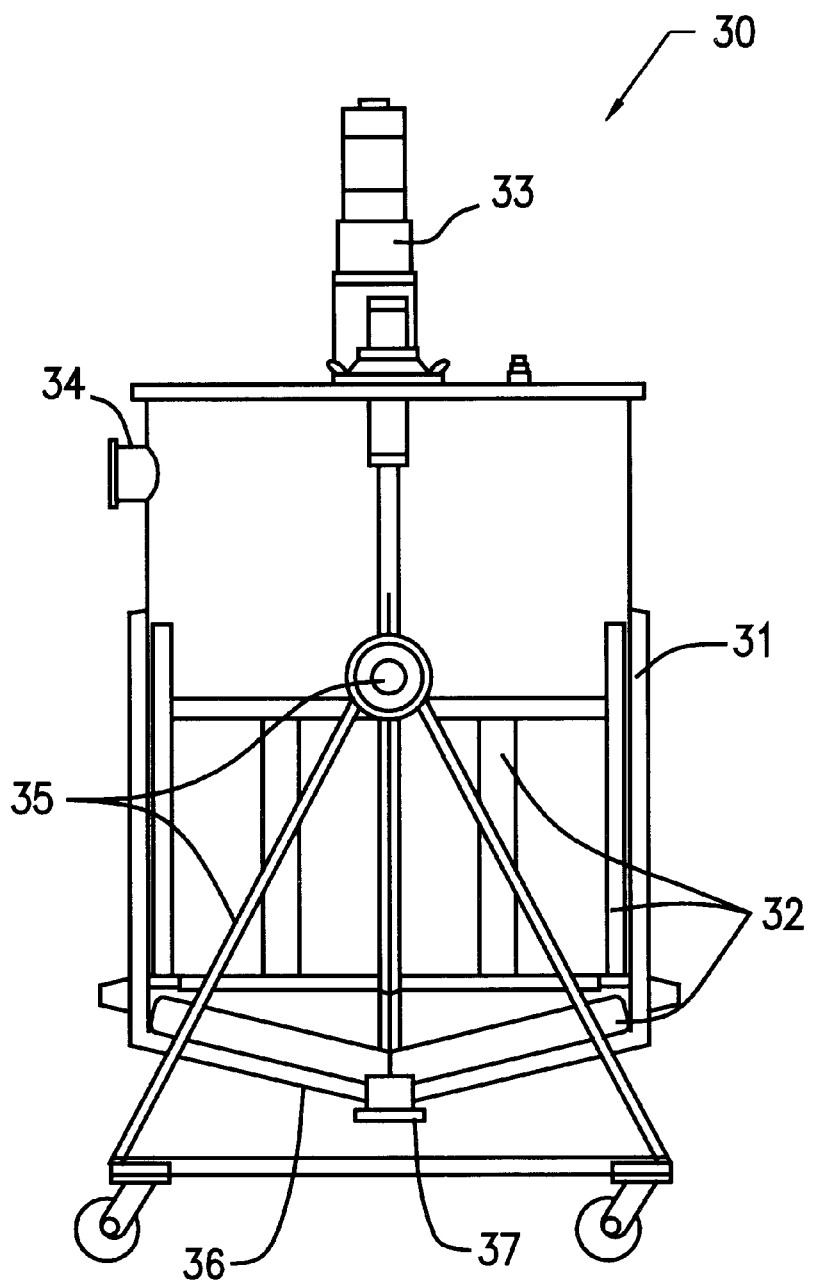

FIG. 3 illustrates an apparatus 30 that may be utilized to process non-aqueous fills that do not contain dissolved and/or suspended solids such as natural and/or synthetic vitamin E. The apparatus is equipped with a heating/cooling jacket 31 to approximately two-thirds of the vessel height; to apply heat primarily to the aqueous phase during processing in the event the non-aqueous fill being processed is thermally sensitive and to apply cooling to primarily the aqueous phase to solidify the aqueous phase. The apparatus is also equipped with a sweep mixer 32 designed in such a manner to perform a variety of functions including, but not limited to, dislodging molten gelatin from the walls and bottom of the vessel, homogenizing the aqueous phase for ease of processing/separating the aqueous phase, and dislodging residual non-aqueous fill trapped in residual molten gelatin. Additionally, the preferred mixer motor 33 is designed to operate at low speed. The apparatus is equipped with a side discharge 34 at about three-quarters the vessel height and swivel arms 35 on each side of the vessel to allow the non-aqueous phase to be poured from the top of the vessel, after the aqueous phase has been solidified, for a very efficient separation and recovery of the non-aqueous phase. The apparatus is also designed with a sloped bottom 36 and bottom center discharge 37 for removing the aqueous phase once the non-aqueous phase is removed.

Alternatively, the apparatus 20 illustrated in FIG. 2, and described above, may be utilized to process non-aqueous fills that do not contain dissolved and/or suspended solids, if solidification of the solvent layer is not preferred or desired.

Referring again to FIG. 1, the deionized water in vessel 2 is heated, with agitation, to a temperature from about 40° C. to 70° C. Once the desired temperature has been achieved the agitation rate is lowered typically to about 5 to 40 rpm and the waste gelatin material containing a non-aqueous fill, typically in the form of capsules, is added to vessel 2 through a conduit 3. The above recited temperature and agitation are maintained until the capsules are at least substantially dissolved, which typically takes from about 15 to 60 minutes, at which time the non-aqueous fill is at least substantially separated from the aqueous phase. Agitation is stopped once there is substantial separation between the non-aqueous fill and the aqueous phase.

Once agitation is stopped, the contents of vessel 2 may be held, while maintaining the above recited temperature range, for about 5 to 30 minutes to complete phase separation prior to physical separation.

Separation may be achieved in any conventional manner including, but not limited to, physical separation through a sight glass or an oil skimmer. The separation may also take place through various mechanical techniques such as, but not limited to, liquid-liquid centrifugation. Alternatively, the lower, gelatin containing aqueous phase may be solidified with cooling and the non-aqueous phase collected from the top by decanting or pouring.

In a preferred embodiment, for non-aqueous fills containing dissolved or suspended solids, the separation is achieved using the apparatus 20 as illustrated in FIG. 2. The lower aqueous phase is separated, using a sight glass, and is conveyed via conduit 4 to an apparatus 5 where it may be further processed to recycle the gelatin, plasticizer and, if applicable, dyes and other water soluble components, or discarded.

The upper, non-aqueous phase is then sent, optionally, via a conduit 6 to a drying apparatus 7 where it may be at least substantially dried using a variety of techniques including, but not limited to, drying agents such as molecular sieves or magnesium sulfate, heating at atmospheric pressure for a given period of time at a given temperature, or heating under vacuum for a given period of time at a given temperature.

Figure 4:
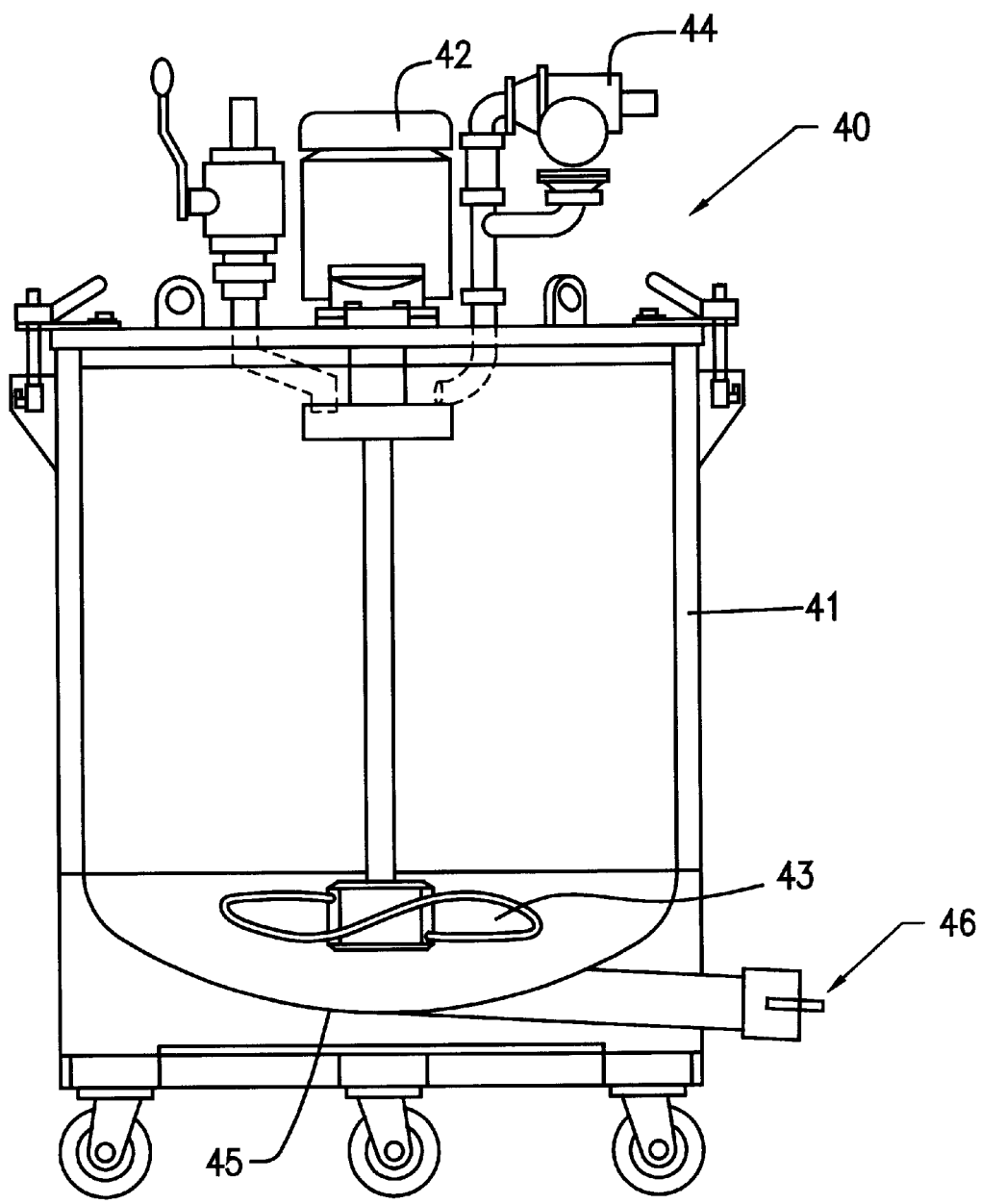

In the preferred embodiment heating under vacuum is employed using a vessel design such as that illustrated in FIG. 4. This method of at least substantially drying the non-aqueous phase is preferred over atmospheric heating to avoid any potential thermal degradation when processing potentially heat sensitive products. Water may be removed at a lower temperature under vacuum conditions than at or about atmospheric conditions. This method is also preferred over drying agents in that no chemical additives are being utilized that may result in contamination of the non-aqueous phase.

FIG. 4 is illustrative of a preferred drying apparatus 7. FIG. 4 shows a vessel 40 of stainless steel construction equipped with a heating/cooling jacket 41, a mixer motor 42 and mixer 43 with a vacuum pump 44 capable of achieving from about 22 inches to 29 inches vacuum. The vessel is constructed to withstand the above recited vacuum range and has a sloped bottom 45 with side discharge 46 emanating from the center of the sloped bottom 45.

Once the non-aqueous phase has been transferred to drying apparatus 7, mixing is started and vacuum is applied typically in the range from about 22 inches to 29 inches. The contents may then be heated to from about 30° C. to 70° C. and held at the above recited vacuum and temperature until the non-aqueous phase is at least substantially dried, usually from about 15 minutes to 2 hours.

Drying without vacuum or the use of drying aids may require periods of 24 hours or longer and temperatures above 100° C.

Once the non-aqueous phase has been at least substantially dried it may be sent via conduit 8 as shown in FIG. 1 to an optional filtration apparatus 9 to at least substantially remove residual particulates. Filtration may be accomplished by a variety of techniques including, but not limited to, microporous bag filters as typically used in the gelatin capsule manufacturing industry.

Alternatively, if the non-aqueous phase does not require drying it may be sent directly to an optional filtration apparatus 9 via a conduit 8A and processed as described above.

The non-aqueous phase may then be collected via a conduit 10 to be reused in the capsule filling process.

By way of illustration, the following examples as shown in Table 1 are given to demonstrate the increased recovery of non-aqueous fills from capsules in accordance with the present invention as compared with a conventional technique; including results of analytical analyses of the recovered non-aqueous fills.

What is claimed is:

1. A method of recovering non-solvent fills from gelatin capsules comprising:
   a) adding the gelatin capsules to a suitable solvent to for including a solvent phase and a non-solvent phase containing said non-solvent fills;
   b) separating the solvent phase from the non-solvent phase containing said non-solvent fills; and
   c) recovering the non-solvent fills.

2. The method of claim 1 wherein the solvent is deionized water.

3. The method of claim 1 wherein the gelatin capsules containing the non-solvent fills are obtained from hard or soft gelatin capsules.

4. The method of claim 1 wherein the amount of the solvent is up to about 5.0 volumes wt/wt.

5. The method of claim 1 wherein step (a) is carried out at a temperature of from about 40 to 70° C.

6. The method of claim 1 further comprising agitating the gelatin capsules and the solvent.

7. The method of claim 6 wherein agitation is performed at from about 5 to 40 rpm.

8. The method of claim 1 comprising performing step (b) by a method selected from physical separation, mechanical skimmer, liquid-liquid centrifugation and combinations thereof.

9. The method of claim 1 wherein step (b) comprising solidifying the solvent phase and decanting or pouring the non-solvent phase from the top of the vessel.

10. The method of claim 1 further comprising removing solvent from the non-solvent phase.

11. The method of claim 10 wherein the method of removing solvent from the non-solvent phase comprises heating the non-solvent phase under vacuum.

12. The method of claim 10 wherein the method of removing solvent from the non-solvent phase comprises heating the non-solvent phase at or about atmospheric pressure.

TABLE 1

| Non-Aqueous Material | Additives | Quantity (g/Kg) of Capsules Recovered | Quantity (g/Kg) of DI Water Used | Prior Art Recovery % | Improved Recovery % | % Assay |
|---|---|---|---|---|---|---|
| CoEnzymeQ10 | Soy oil | 250 g | 500 g | 30 | 89.1 | 105.6 Passes Spec |
| Nat. Vit. E | None | 250 g | 500 g | 50 | 97.3 | 102.8 Passes Spec |
| Syn. Vit. E | None | 250 g | 500 g | 50 | 94.6 | 99.2 Passes Spec |
| CoEnzymeQ10 | Soy oil | 13.8 kg | 27.6 kg | 30 | 97.4 | Not Assayed (1) |
| Syn. Vit. E | None | 77 Kg | 154 Kg | 50 | Not Determined | 98.8 Passes Spec |
| Saw Palmetto | Soy Oil | 250 g | 500 g | 0 | 90.9 | FA = 92.1% Sterols = 0.2% Passes Spec |
| Shark Liver Oil | Soy Oil | 250 g | 500 g | 0 | 100 | 21.7% alkoxyglyoerol-etherlipids Passes Spec |
| Ginseng | Soy Oil | 250 g | 500 g | 0 | 95.7 | Passes TLC |
| MultiComponent | Soy Oil | 250 g | 500 g | 0 | 76.7 | EPA141.8 mg DHA104.1 mg DLA95.4 mg Passes Spec |

(1) Larger scale evaluated for percent recovery only. Assay results for CoEnzymeQ10 achieved in the first example above would also be expected for large scale recoveries.

13. The method of claim 10 wherein the method of removing solvent from the non-solvent phase comprises treating the non-solvent phase with a drying agent.

14. The method of claim 11 wherein the vacuum is from about 22 to 29 inches.

15. The method of claim 11 wherein the non-solvent phase is heated to a temperature of from about 30° to 70° C.

16. The method of claim 14 wherein the non-solvent phase is heated to temperature of from about 40° C. to 105° C.

17. The method of claim 13 wherein the drying agent is selected from the group consisting of molecular sieves and magnesium sulfate.

18. The method of claim 1 further comprising filtering the non-solvent phase to remove residual particulate matter.

19. The method of claim 1 further comprising recovering gelatin from the solvent phase.

20. The method of claim 19 further comprising recovering at least one other material from the solvent phase selected from the group consisting of plasticizers and dyes.

* * * * *

UNITED STATES PATENT AND TRADEMARK OFFICE
CERTIFICATE OF CORRECTION

PATENT NO. : 6,361,802 B1
DATED : March 26, 2002
INVENTOR(S) : William J. Schmidt It is certified that error appears in the above-identified patent and that said Letters Patent is hereby corrected as shown below:

Column 6,
Line 4, cancel "for" insert -- form a mixture --; and
Line 27, cancel "comprising" insert -- comprises --.

Signed and Sealed this

Twenty-third Day of December, 2003

JAMES E. ROGAN
*Director of the United States Patent and Trademark Office*